United States Patent [19]

Mericle et al.

[11] 4,450,840

[45] May 29, 1984

[54] LIGATING CLIP WITH FLANGED BASE HAVING A RECESSED ENGAGING FACE

[75] Inventors: Robert W. Mericle, Lebanon; James A. Transue, Union, both of N.J.

[73] Assignee: Ethicon, Inc., Somerville, N.J.

[21] Appl. No.: 352,834

[22] Filed: Feb. 26, 1982

[51] Int. Cl.³ ............................................. A61B 17/12
[52] U.S. Cl. .................................... 128/325; 128/346; 227/DIG. 1
[58] Field of Search ................... 128/325, 326, 334 R, 128/335, 335.5, 346; 227/DIG. 1, DIG. 1 B, DIG. 1 C, 19, 117, 125; 29/243.56; 72/410

[56] References Cited

U.S. PATENT DOCUMENTS

| 4,294,355 | 10/1981 | Jewusiak et al. | 128/346 X |
| 4,361,229 | 11/1982 | Mericle | 128/325 X |
| 4,380,238 | 4/1983 | Colucci et al. | 128/325 X |

FOREIGN PATENT DOCUMENTS 2054026  2/1981  United Kingdom ................ 128/326
2069848  9/1981  United Kingdom ................ 128/326

Primary Examiner—C. Fred Rosenbaum
Assistant Examiner—Michelle N. Lester
Attorney, Agent, or Firm—Robert L. Minier

[57] ABSTRACT

A ligating clip is provided with first and second legs joined at their proximal ends by a resilient hinge to define the rear end of the clip and spaced at their distal ends at the front of the clip with the legs having latch means at the distal ends for holding the clip closed in clamping engagement about tissue when the legs are squeezed together. The clip has a base extending along a portion of the first leg and the base terminates short of the distal end in a front face. Flanges are provided on a portion of the base and extend rearwardly from the front face and terminate short of the first leg proximal end. The flanges extend laterally outwardly beyond the sides of the first leg. The portion of the base that extends rearwardly from the flanges to the proximal end of the clip first leg has a width not greater than the width of the first leg.

12 Claims, 16 Drawing Figures

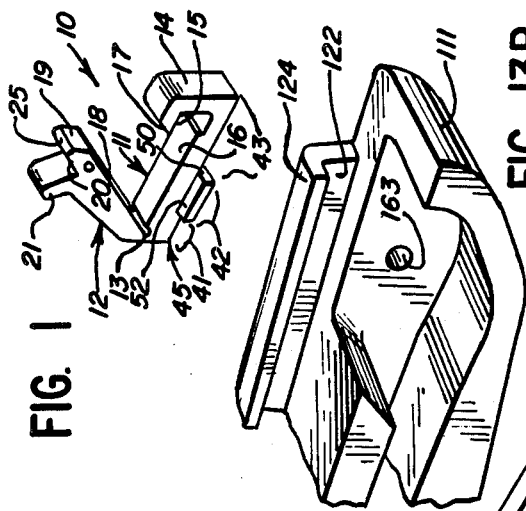
FIG. 1
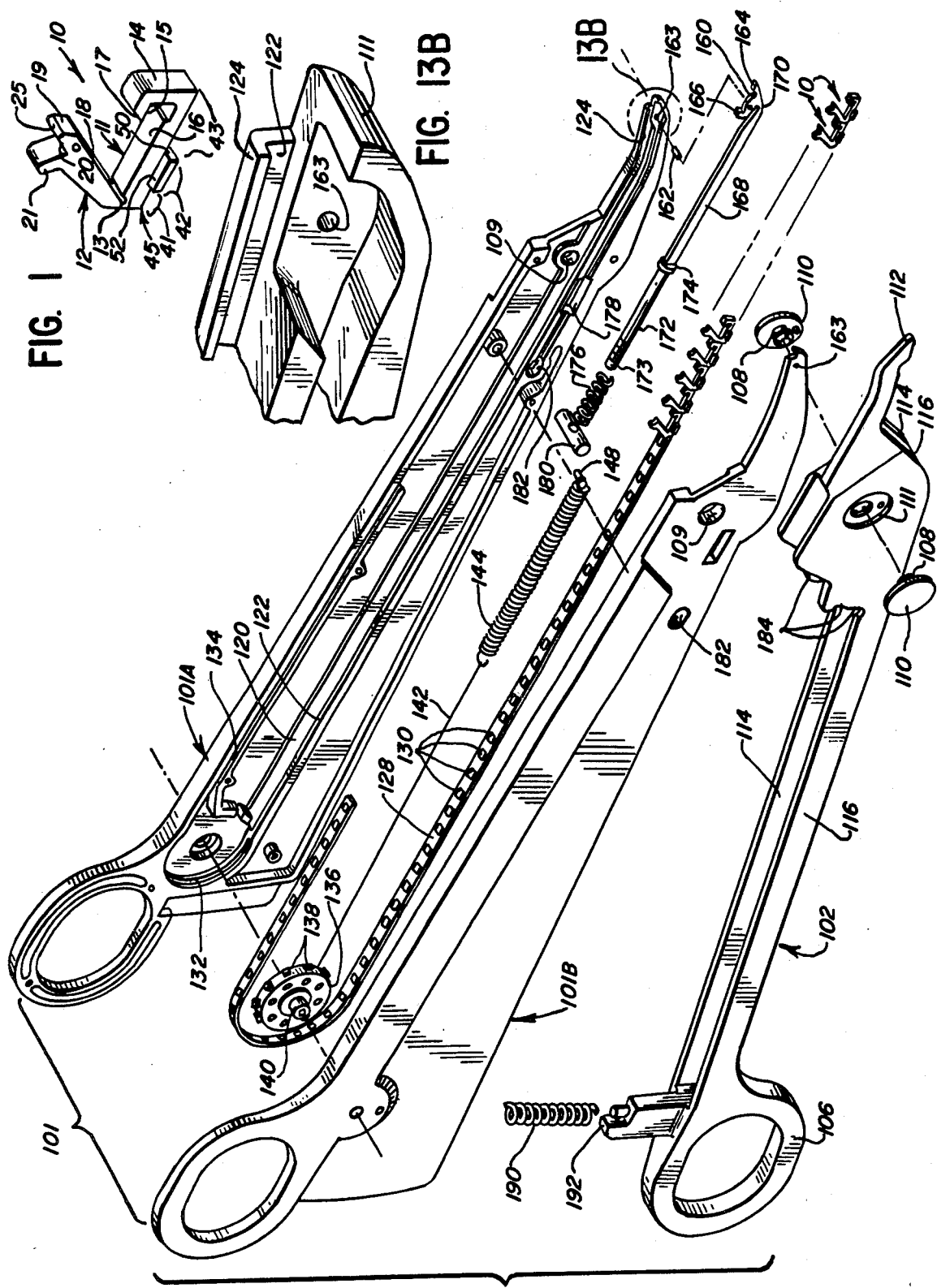
FIG. 13A
FIG. 13B

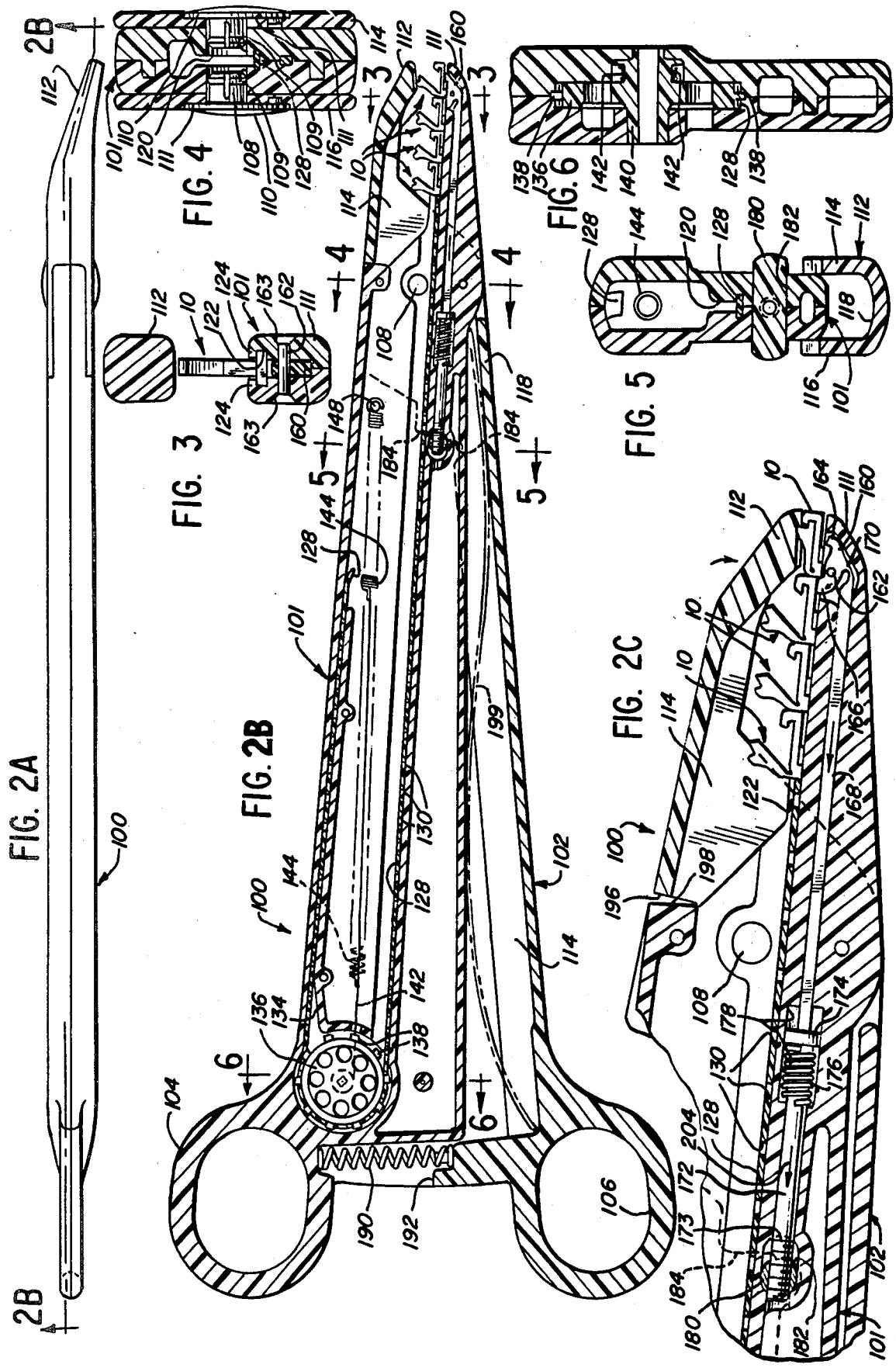

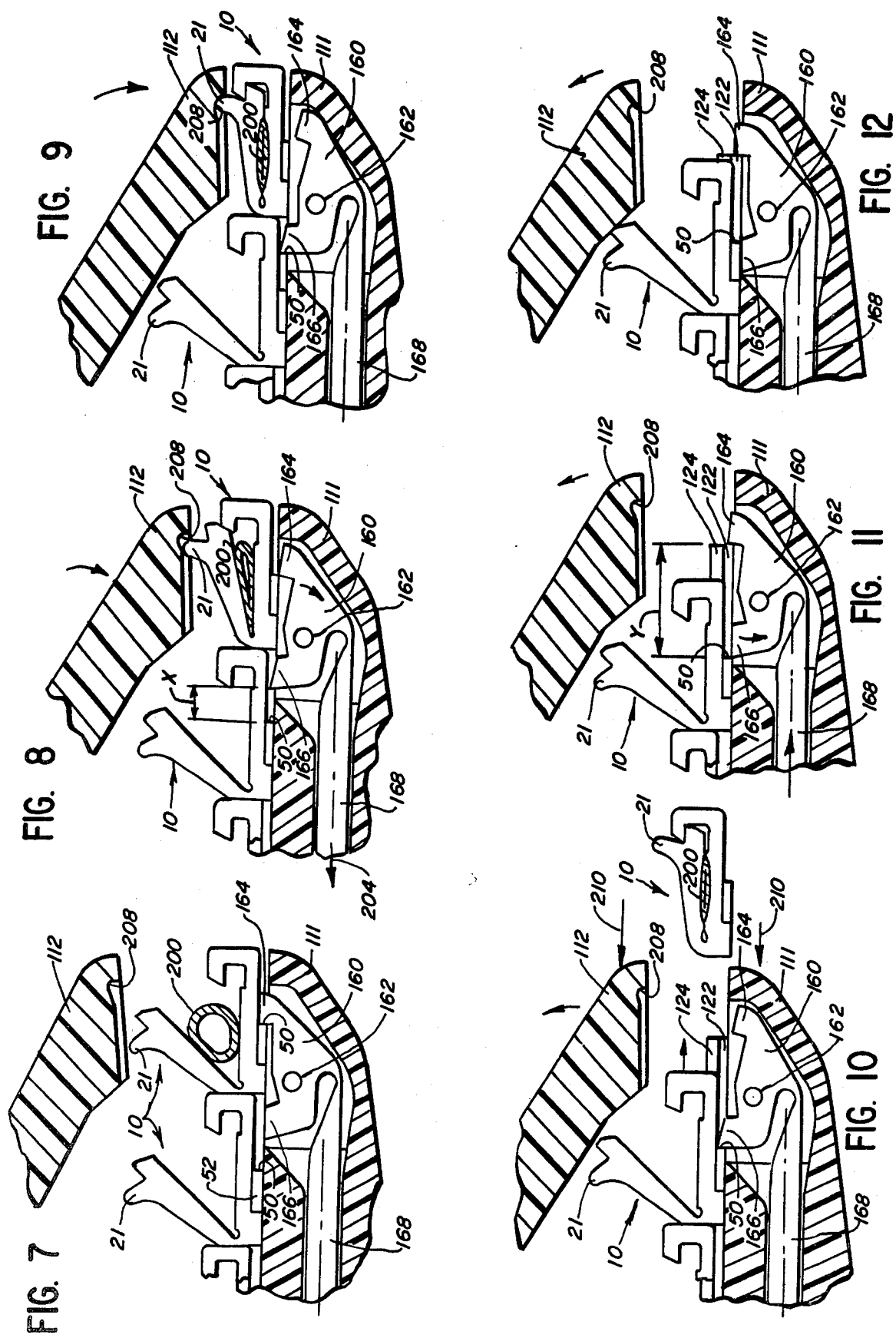

LIGATING CLIP WITH FLANGED BASE HAVING A RECESSED ENGAGING FACE

TECHNICAL FIELD

This invention relates to hemostatic or ligating clips adapted to be applied with surgical instruments to tissue, blood vessels, and the like.

BACKGROUND OF THE INVENTION

Clips have been devised for clamping or strangulating various organs, vessels, and other tissue. Clips have been developed for use specifically in strangulating blood vessels in the human body. Such clips are known as hemostatic or ligating clips. The clips may be fabricated from absorbable or nonabsorbable polymeric materials as well as from metal.

A ligating clip is typically C-shaped, U-shaped, or V-shaped with two spaced-apart or diverging legs connected together at one end in a manner that permits the clip to be squeezed together so that the legs of the clip may be clamped around the tissue or blood vessel so as to tightly constrict the tissue or blood vessel. This prevents a substantial amount of fluid from passing through the tissue or blood vessel from one side of the closed clip to the other side of the closed clip.

Typically, the clip is made of a material and/or has a configuration that enables the clip, once it has been forced closed, to maintain the closed orientation without outside intervention. For example, if the clip is made from a metal material, the clip can be deformed to the closed position. If the clip is made from a thermoplastic material, the legs may be connected by a resilient hinge portion and the distal ends of the legs may be provided with latch means for holding the legs together in a closed position when the legs of the clip are squeezed together around the tissue or blood vessel.

Various novel ligating clips are disclosed in copending U.S. patent applications assigned to the assignee of the present invention: Ser. Nos. 208,368, filed on Nov. 19, 1980; 276,131, filed on June 22, 1981; 277,582, filed on June 26, 1981; 277,454, filed on June 26, 1981; 282,461, filed on July 13, 1981; and 296,672, filed on Aug. 27, 1981.

Some types of surgical clips have been proposed wherein one of the legs of the clip is especially adapted for being engaged by, and supporting the clip in, an applier instrument. See, for example, U.S. Pat. Nos. 3,780,416 and 3,882,854 which each disclose an asymmetric clip having two differently shaped legs with one of the legs being adapted to be received in a carrier or lower jaw of an applier instrument.

It would be desirable to provide a ligating clip which could be easily applied by an instrument to tissue, such as a blood vessel and the like. Further, it would be desirable to provide such a clip with a configuration that would permit a plurality of such clips to be loaded into, and contained within, the instrument for applying the clips.

Further, it would be beneficial if the clip could be provided with a configuration that would permit the clip to be easily accommodated in the instrument and to be moved forward within the instrument to the clip applying jaws of the instrument by a relatively simple and trouble free mechanism.

Also, it would be advantageous if such a clip had a configuration which would permit it to be restrained within the clip applying instrument and to be guided by the clip applying instrument to the jaws of the instrument.

A variety of instruments for applying certain types of surgical clips have been developed or proposed in the past. A number of such instruments are discussed and disclosed in the copending patent application Ser. No. 208,368, filed on Nov. 19, 1980. Such instruments typically include a magazine or cartridge which may or may not be disposable and which holds a plurality of clips. The clips are supplied from the cartridge to jaws of the instrument one at a time for application to the tissue or blood vessel.

U.S. Pat. No. 3,006,344 discloses an instrument for applying a ligating clip to a blood vessel. The clip is formed of flat metal or like stock and has a pair of legs extending outwardly in a generally V-shape. The clips are arranged in two parallel grooves in a magazine. A slide is positioned in each groove and is urged by a suitable conventional spring to advance the clips along the magazine toward the jaws. The clips are arranged in each row with the distal end of one of the legs of one clip abutting the rear connecting hinge portion of the next adjacent clip.

U.S. Pat. No. 3,753,438 discloses an applicator for applying clips to suturing thread during the suturing of skin wounds. The clips are carried in a cartridge in the instrument. A clip is forced forwardly from the cartridge to a position between the instrument jaws by a slide which is operated by a handle. After the clip is positioned within the jaws, the handles of the instrument are squeezed together to squeeze the clip legs together.

SUMMARY OF THE INVENTION

A novel ligating clip is provided that is particularly well-suited for use with a scissors-type medical instrument is provided for repeatedly applying a plurality of the ligating clips seriatim about tissue.

A preferred embodiment of the clip of the present invention is fabricated from a thermoplastic material. The clip typically has two legs that are connected together at one end of the clip and that are adapted to assume an initial open or spread apart configuration at the other end.

The clip includes first and second legs joined at their proximal ends by a resilient hinge to define the rear end of the clip and spaced apart at their distal ends at the front of the clip with the legs having latch means at the distal ends for holding the clip closed in clamping engagement about tissue when the legs are squeezed together.

In a preferred embodiment, the clip has a base extending along a portion of said first leg. The base terminates short of the distal end of the first leg in a front face whereby an open recess is defined adjacent the front face of the base below the first leg. With one type of applier instrument, this permits positioning of an escapement mechanism of the instrument against the face.

Flanges are provided on a portion of the base. The flanges extend rearwardly from the front face and terminate short of the first leg proximal end. The flanges extend laterally outwardly beyond the sides of the first leg. With one type of applier instrument, the flanges function as guide means for engaging portions of the instrument.

The portion of the base that extends rearwardly from the flanges to the proximal end of the clip first leg has a width not greater than the width of the first leg. With one type of applier instrument, such a base structure facilitates ejection of the latched closed clip from the instrument when the escapement is withdrawn.

The first leg of the clip may be alternatively described as having (1) a rear section extending from the hinge, (2) a front section extending from the distal end of the first leg, and (3) a middle section connecting the front and rear sections. The base can then be regarded as extending along the rear and middle sections of the first leg and terminating in a front face below the juncture of the middle and front sections of the first leg so that the first leg front section extends forwardly beyond the base front face to define an open recess adjacent the base front face below the first leg front section. The portion of the base along the first leg rear section has a width not greater than the width of the first leg. The base flanges extend laterally outwardly beyond the sides of the first leg along the length of the clip first leg middle section.

Numerous other advantages and features of the present invention will become readily apparent from the following detailed description of the invention and an embodiment thereof, from the claims, and from the accompanying drawings.

BRIEF DESCRIPTION OF THE DRAWINGS

In the accompanying drawings forming part of the specification, and in which like numerals are employed to designate like parts throughout the same, FIG. 1, on the sheet of drawings with FIGS. 13A and 13B, is a greatly enlarged, perspective view of an open ligating clip of the present invention;

FIG. 2A is a side view of the preferred embodiment of the medical instrument that can be used for repeatedly applying a plurality of ligating clips of the type illustrated in FIG. 1;

FIG. 2B is a cross-sectional view taken generally along the planes 2B—2B in FIG. 2A and showing the instrument jaws open;

FIG. 2C is a greatly enlarged, fragmentary, cross-sectional view similar to FIG. 2B but showing the instrument latching a clip closed;

FIG. 3 is a greatly enlarged, cross-sectional view taken generally along the planes 3—3 in FIG. 2B;

FIG. 4 is a greatly enlarged, cross-sectional view taken generally along the plane 4—4 in FIG. 2B;

FIG. 5 is a greatly enlarged, cross-sectional view taken generally along the plane 5—5 in FIG. 2B;

FIG. 6 is a greatly enlarged, fragmentary, cross-sectional view taken generally along the plane 6—6 in FIG. 2B;

FIGS. 7-12 are greatly enlarged, fragmentary, cross-sectional views of the front jaw region of the instrument showing the sequence of operation of the instrument;

FIG. 13A is an exploded, perspective view of the instrument; and

FIG. 13B is a greatly enlarged, fragmentary, perspective view of one of the two mating pieces that form the lower jaw in the region indicated by the dashed line circle labeled 13B in FIG. 13A.

DESCRIPTION OF THE PREFERRED EMBODIMENT

While this invention is susceptible of embodiment in many different forms, there is shown in the drawings and will herein be described in detail a preferred embodiment of the invention. It should be understood, however, that the present disclosure is to be considered as an exemplification of the principles of the invention and is not intended to limit the invention to the embodiment illustrated.

The precise shapes and sizes of the structural parts of the novel clip and clip applier instrument herein described are not essential to the invention unless otherwise indicated. Unless otherwise indicated, the particular shapes and sizes are shown to best illustrate the principles of the invention.

A preferred embodiment of the ligating clip 10 of the present invention is illustrated in FIG. 1. The clip 10 has a first leg 11 and a second leg 12. The legs 11 and 12 are joined at their proximal ends at the rear of the clip by a resilient hinge, hinge means, or hinge section 13 which permits the legs 11 and 12 to be pivoted toward each other to a closed position. Until the clip 10 is closed in a manner to be described in detail hereinafter, the hinge 13 has sufficient resiliency to maintain the legs 11 and 12 in the angled open position illustrated in FIG. 1.

The first leg 11 terminates at the distal end thereof in a hook member 14 having a downwardly facing inner face 15 substantially parallel to an upwardly facing inner face 16 of the first leg 11 and forming an acute angle with an end face 17.

The second leg 12 terminates at the distal end thereof in an end face 19 which forms an obtuse angle with an inner face 18 of the leg 12. The end face 19 of the second leg 12 is formed at an angle relative to a squared off face 25 which forms a substantially right angle with an upper surface 20.

The length and width of the face 16 of the first leg 11 and of the face 18 of the second leg 12 are substantially equal, and the face 15 of the hook member 14 is spaced from face 16 of the leg 11 by a distance corresponding to the thickness of the leg 12 between the plane of inner face 18 and the plane of upper surface 20.

When the legs 11 and 12 are pivoted about hinge 13 to bring the faces 18 and 16 into opposition, the hook member 14 is deflected by the end face 19 of the second leg 12 until the distal end of the second leg 12 snaps under the hook member 14 and is thereby locked in place. Such a closure of the clip 10 is illustrated in FIG. 9 wherein the clip 10 is shown latched or locked closed about a blood vessel 200.

The end face 17 of the hook member 14 and the end face 19 of the second leg 12 are angled as illustrated to facilitate the passage of the second leg 12 past the hook member 14 during closure of the clip 10.

When the clip 10 is closed over a blood vessel 200 (as illustrated in FIG. 9), the surfaces 16 and 18 engage and compress the vessel 200 to close the lumen thereof. The surfaces 16 and 18 may be smooth as illustrated in FIG. 1, or may be provided with ridges or grooves to increase vessel holding power.

The first leg 11 may also be undercut at the juncture of the hook member 14 and the surface 16 as illustrated in FIG. 1 to increase deflectability of the hook member 14 and increase the space between the hook member 14 and the leg 11, thereby compensating for any inward deflection of the hook member 14 during closure of the clip which might reduce the clearance between the hook member surface 15 and the first leg surface 16 and otherwise interfere with the latching of the clip 10.

The clip 10 may also include an outside cylindrical boss 21 extending across the width of the second leg 12 near the distal end thereof. The boss 21 is spaced from surface 25 a distance sufficient to permit full engagement of the hook member 14 by the leg 12 when the clip 10 is in a closed and latched position.

The clip 10 also has a novel base 45 extending along a portion of the first leg 11. The base 45 terminates short of the distal end of the first leg 11 in a front face 50 whereby an open recess is defined adjacent the front face 50 and below the first leg 11 to permit positioning of an escapement mechanism of the instrument against the face 50. Such an escapement mechanism is described in detail hereinafter.

Flanges 52 are provided on a portion of the base 45. The flanges 52 extend rearwardly from the front face 50 and terminate short of the first leg proximal end. The flanges 52 extend laterally outwardly beyond the sides of the first leg 11 to function as guide means for engaging portions of the instrument. The portion of the base 45 that extends rearwardly from the flanges 52 to the proximal end of the clip first leg 11 has a width not greater than the width of the first leg 11 to facilitate ejection of the latched closed clip from the instrument when the escapement is withdrawn.

Depending on the type of instrument used to apply the clip 10 to tissue, the hook member 14 may be provided on the second leg 12 instead of on the first leg 11 with the base 45. Further, other suitable latching structures (not illustrated) may be provided at the ends of the clip legs. The illustrated hook member 14 on leg 11 and the cooperating end of the other leg 12 are just one example of a suitable latching means structure.

The first leg 11 of the clip 10 may be alternatively described as having three sections: a rear section 41, a middle section 42, and a front section 43 as best illustrated in FIG. 1. The rear and front sections 41 and 43, respectively, are connected by the middle section 42.

In terms of the above-identified three leg sections, the base 45 can be regarded as extending along the first leg 11 and terminating in the front face 50 below the juncture of the leg middle section 42 and the leg front section 43. Thus, the first leg front section 43 extends forwardly beyond the base front face 50 to define an open recess adjacent the base front face 50 and below the first leg front section 43.

The clip flanges 52 can be regarded as extending along the length of the clip first leg middle section 42 and as extending laterally outwardly beyond the sides of the first leg 11.

The portion of the base 45 along the first leg rear section 41 extends rearwardly from the flanges 52 but has a width that is not greater than the width of the first leg 11. The portion of the base 45 along the first leg rear section 41 has a generally right rectangular prism configuration. Similarly, the portion of the base 45 with the flanges 52 along the first leg middle section 42 has a generally right rectangular prism configuration.

Portions of the clip first leg 11 and of the base 45 are adapted to function as guide means for engaging portions of the instrument and for being engaged by the escapement mechanism of the instrument. A preferred embodiment of such an instrument is next described in detail.

Each of the above-described novel clip structures, when fabricated from a suitable thermoplastic material, is biased to the open position by the resilient hinge portion. Thus, if force is applied to the distal ends of the legs of the open clip so as to move the legs toward one another (but not far enough to latch the clip), then upon removal of the force from the clip legs, the clip legs will return to the substantially fully open orientation.

It is believed that this phenomenon can be used to advantage in certain types of clip applier instruments for guiding and holding the clip in the instrument. Specifically, the legs of the clip may be deflected inwardly toward one another a small amount in a magazine, guide channel, or jaw structure of a clip applier instrument. Owing to the resilience of the hinge joining the two legs, the two legs will exert a force outwardly against the magazine, channel, or jaw structure to thereby provide a small friction holding force which may serve to help maintain the clip in the proper orientation or position within the instrument.

The above-described action of the resilient hinge plastic clip is in contrast with conventional ligating clips fabricated from relatively small diameter wire-like stock. Such metal clips can tolerate substantially no inward deflection of the legs without undergoing permanent deformation. Consequently, such metal clips exhibit no useful degree of resiliency and thus do not have the same inherent capability for providing the frictional holding force that is found in the above-described type of plastic clip. Of course, if the clip is to be applied with a type of instrument that does not make use of the resilient hinge capability of the clip, then the clip may be fabricated from any suitable material with the novel base structure, but without a resilient hinge.

A scissors-type medical instrument 100, generally illustrated in FIGS. 2A and 2B, is adapted for holding a supply of the above-described ligating clips 10 of the present invention and for applying the clips seriatim to tissue.

The instrument 100 has a first handle 101 and a second handle 102. The first handle 101 has a finger or thumb ring 104 and the second handle also has a finger or thumb ring 106. As best illustrated in FIG. 13A, the first handle 101 includes two mating pieces or halves 101A and 101B which are secured together by suitable means, such as by screws (not illustrated).

The first and second handles 101 and 102 are mounted together for pivotal movement about a pivot axis defined by two spaced-apart coaxial shafts 108. Each shaft 108 has an exterior head or cover 110 which is received in a cavity 111 in each side of handle 102 (FIGS. 4 and 13A). The distal end of each shaft 108 is press-fitted into an aperture 109 in the side of the handle half 101A or 101B (FIGS. 4 and 13A).

Each handle 101 and 102 extends forwardly beyond the pivot axis shafts 108 to form a clip-closing jaw—a first handle lower jaw 111 and a second handle upper jaw 112 as illustrated best in FIGS. 2B and 13A. As can best be seen in FIG. 2A, the jaws 111 and 112 are preferably curved toward one side.

As best illustrated in FIGS. 2B, 5 and 13A, the second handle 102 has a pair of spaced-apart sidewalls 114 and 116 projecting upwardly from a bottom wall 118 to define a generally U-shaped configuration. Toward the front of the instrument 100, in the region below the pivot shafts 108, the second handle bottom wall 118 terminates but the sidewalls 114 and 116 continue upwardly. As best illustrated in FIG. 13A, the sidewalls 114 and 116 project upwardly above the pivot shafts 108 and merge to form the second handle upper jaw 112.

The first handle halves 101A and 101B define a chamber, channel, or guideway 120 as best illustrated in FIGS. 4, 5, and 13A. The guideway 120 receives a plurality of the open clips 10 in end-to-end relationship with the distal end of the first leg of one clip abutting the hinge end of the next forwardly adjacent clip. The clips can be moved forwardly along the guideway 120 by means described hereinafter in detail.

As best illustrated in FIGS. 3 and 13A, the first handle 101 defines a bottom channel 122 for receiving the clip base and base flanges 52 of each clip 10. The instrument 100 includes inwardly projecting flanges 124 above the bottom channel 122. The flanges 124 of the guideway 120 function to engage the base flanges 52 of the clips when the instrument 100 is tilted or turned to any position other than the horizontal position illustrated in FIG. 2B. The flanges 124 thus function to retain the clips within the instrument 100. The channel 122, in cooperation with the flanges 124, permits sliding movement of the clips 10 forwardly along the guideway 120.

The clips 10 are moved forwardly along the guideway 120 to the region of the jaws 111 and 112 by a novel pusher member 128. The pusher member 128 is preferably a flexible, perforated tape defining a plurality of equally spaced apertures 130 extending along the length of the tape. Preferably, each aperture 130 has a substantially rectangular configuration.

The flexible pusher member tape 128 preferably has a generally rectangular cross-section and is adapted to be received within the channel 122 behind the last clip of the row of clips 10 in the instrument first handle 101. Preferably a trailing portion of the tape 128 extends around an approximately semi-circular portion of the periphery of a chamber 132 (FIG. 13A) in the rear portion of the first handle 101 and is received within an upper tape slot 134 located above, and substantially parallel to, the channel 122.

The instrument 100 further preferably includes a means for feeding the tape 128 forwardly along the channel 122 at the bottom of the guideway 120 to move the row of clips 10 forwardly along the first handle 101 to the jaws 111 and 112. Specifically, a sprocket wheel 136 is mounted for rotation within the chamber 132 relative to the first handle 101. The sprocket wheel 136 has a plurality of circumferentially spaced and radially outwardly projecting pins 138 which are adapted to engage the perforations or apertures 130 in the tape 128.

As best illustrated in FIGS. 6 and 13A, the sprocket wheel 136 includes a hub 140 for rotating with the wheel 136 relative to the first handle 101. A flexible cord 142 is wrapped or wound around the hub 140 and is secured to one end of a tension spring 144 disposed within the first handle 101. The other end of the tension spring 144 is secured at a post or pin 148 (FIGS. 2B and 13A) to the first handle 101. The spring 144 thus pulls the cord 142 from the hub 140 to thereby rotate the hub 140 and the wheel 136 to drive the tape 128 forwardly in the clip guideway bottom channel 122.

In FIG. 2B, the spring 144 is shown in dashed line in the initial position when the instrument 100 is fully loaded with clips 10 and when the spring 144 is at a maximum elongation. When the instrument 100 is fully loaded, the clips 10 fill up almost the entire length of the guideway 120 along the first handle 101 and only a short leading end portion of the flexible tape 128 projects into the guideway bottom channel 122 behind the last clip. Thus, a trailing portion of the tape 128 may initially project out of the upper tape slot 134 and may be coiled within the first handle 101. As the clips are applied by the instrument (in a manner to be described hereinafter), the spring 144 continuously urges the sprocket wheel 136 to rotate and advance the tape 128 forward along the bottom channel 122 of the first handle 101. As this occurs, the spring 144 gradually relaxes and the length of the spring 144 approaches a minimum extension length which is illustrated in solid line in FIG. 2B.

A novel mechanism is provided for 1) preventing the clips 10 from being pushed out of the end of the jaws 111 and 112 until after the jaws are actuated and 2) ensuring that only one clip at a time is properly latched closed about a blood vessel and discharged from the instrument 100. As best illustrated in FIGS. 2C, 3 and 13A, an escapement member 160 is mounted for pivotal, rocking movement about a cylindrical shaft 162 within the first handle lower jaw 111 below the clip guideway channel 122. The shaft 162 is disposed in the jaw 111 with its longitudinal axis generally parallel to the longitudinal axis of the shafts 108 about which the handles 101 and 102 pivot.

As best illustrated in FIGS. 13A and 13B, each half 101A and 101B of the first handle 101 defines an aperture 163 for receiving an end of the pivot shaft 162. The rocker member 160 is adapted to be pivoted or rocked in the first handle lower jaw 111 between a first orientation illustrated in FIG. 2B and a second orientation illustrated in FIG. 2C.

The escapement member 160 has a forward protuberance 164 adapted to project in front of the guideway channel 122 to engage the front face 50 of a base of a clip 10 to prevent passage of the engaged clip therepast when the escapement member 160 is in the first orientation (FIG. 2B). The escapement member 160 also has the rearward protuberance 166 as best illustrated in FIGS. 2C and 13A. The rearward protuberance 166 is spaced rearwardly of the forward protuberance 164 by an amount greater than the length of the base of a clip 10 (i.e., greater than the length of the first leg rear section 41 and the first leg middle section 42 as illustrated in FIG. 1). The rearward protuberance 166 is adapted to project into the guideway lower channel 122 to engage the front face 50 of a base of the next rearwardly adjacent clip 10 to prevent the passage of that clip therepast when the escapement member 160 is in the second orientation (FIG. 2C).

As best illustrated in FIGS. 2C and 13A, a rod 168 is hingedly connected to the bottom of the escapement member 160 and extends rearwardly from the escapement member 160 along the first handle 101. In the illustrated preferred embodiment, the escapement member 160 and the rod 168 are integrally molded from a suitable thermoplastic polymer material as a unitary assembly including a flexible or living hinge designated generally by reference numeral 170 in FIGS. 2C and 13A. Of course, it is to be realized that the escapement member 160 and rod 168 need not be fabricated as a unitary piece and may be connected together by any suitable hinge or pivot structure.

The rod 168 has a distal end portion 172 which is generally cylindrical and is threaded at 173. A flange 174 is provided inwardly of the threads 173 at the inner end of the cylindrical portion 172 of the rod 168. A spring 176 is disposed on the rod cylindrical portion 172 and is received in a cavity 178 for biasing the rod 168 forwardly to pivot the escapement member 160 about the pivot shaft 162 into the first orientation to prevent the passage of a clip from the instrument jaws.

A cylindrical cam follower 180 is threadingly engaged with the threads 173 at the distal end of the cylindrical portion 172 of rod 168 and projects laterally at an angle, preferably 90 degrees, relative to the longitudinal axis of the rod 168. The ends of the cylindrical cam follower 180 are disposed within an elongate cavity 182 within the first handle 101. The elongate cavity 182 is open at either end to permit the distal ends of the cylindrical cam follower 180 to project outwardly beyond the sides of the first handle 101 as best illustrated in FIG. 5.

As best illustrated in FIGS. 2C, 5, and 13A, the second handle 102 defines a cam or cam surface 184 for engaging and moving the cam follower 180. Specifically, the second handle sidewalls 116 and 114 define a stepped cam surface 184 that has a configuration to urge the cam follower 180, and hence the rod 168, rearwardly when the handles 101 and 102 are moved toward one another a sufficient amount so as to squeeze together and latch closed the front clip in the row as illustrated in FIG. 2C. This causes the escapement member 160 to be pivoted to the second orientation wherein the forward protuberance 164 is retracted below the guideway channel 122 to permit the discharge of the clip.

The handles 101 and 102 are normally urged apart to an open position illustrated in FIG. 2B by a helical compression spring 190 disposed between the first handle finger ring 104 and the second handle finger ring 106. When the handles 101 and 102 are squeezed together, overcoming the biasing effect of the spring 190, the closure movement is limited by an abutment member 192 on the second handle finger ring 106 which engages the first handle finger ring 104.

On the other hand, the handles 101 and 102 cannot be opened any further than shown in FIG. 2B. This is because an abutment face 196 (FIG. 2C) behind the upper jaw 112 of the second handle 102 engages an abutment 198 on the first handle 101 above the pivot shafts 108.

The handles 101 and 102 may be biased to the open position illustrated in FIG. 2B by means other than the helical compression spring 190. For example, a leaf-type spring 199 may be disposed within the second handle 102 as illustrated in dashed lines in FIG. 2B. Such a leaf-type spring 199 would be contained between the sidewalls 114 and 116 of the second handle 102 and would have a portion bearing against the first handle 101 to bias the first and second handles apart.

The sequence of operation of the instrument 100 will next be described in detail with reference to FIGS. 2B, 2C and 7-12. When the instrument 100 is in the fully opened position illustrated in FIG. 2B, the escapement member 160 is in the first orientation to engage the front face 50 of the front clip 10 in the row of clips. The same orientation is shown in the enlarged view in FIG. 7 wherein the front clip 10 is shown disposed within the jaws 111 and 112 in an open position adjacent a blood vessel 200.

When the jaws are initially fully opened as illustrated in FIGS. 2B and 7, the front clip 10 is fully opened, but the upper leg of the clip is not in contact with the upper jaw 112. However, the clip base flanges 52 are of course disposed within the guideway lower channel 122 so that the clip is retained in the jaw region by the flanges 124 (FIG. 3). Also, when the open front clip 10 is in the position illustrated in FIG. 7, the clip base front face 50 is engaged by the forward protuberance 164 of the escapement member 160 and further forward movement of the clip is thus prevented. Although the rearward protuberance 166 of the escapement member is retracted out of the guideway below the next rearwardly adjacent clip, the front end of that next rearwardly adjacent clip abuts the hinge portion of the front clip. All of the remaining clips are similarly disposed in end-to-end engagement back to the last clip which is urged forwardly by the flexible tape 128 (FIG. 2B).

FIG. 8 illustrates the jaw region of the instrument as the jaws 111 and 112 begin to close against the front clip 10. The jaws 111 and 112 are moved together by pivoting the instrument handles 101 and 102 (FIG. 2B) toward one another. When the handles 101 and 102 are moved toward one another a sufficient amount, the cam surfaces 184 (FIGS. 2B, 2C, and 13A) urge the cylindrical cam follower 180 rearwardly in the cavity 182. This pulls the rod 168 rearwardly in the direction of the arrow 204 as best illustrated in FIGS. 2C and 8. The rearward movement of the rod 168 causes the escapement member 160 to pivot (in the clockwise direction as viewed in FIG. 8) to withdraw the forward protuberance 164 below the front of the clip guideway and to raise the rearward protuberance 166 into the clip guideway. At the point in the operating sequence illustrated in FIG. 8, the front clip 10 cannot be discharged from the instrument because the top of the clip, namely the clip protuberance 21, is engaged by the upper jaw 112 and because the clip base flanges are still retained in the clip guideway channel 122 by the flanges 124.

When the instrument handles are fully closed, the spacing between the jaws 111 and 112 is at a minimum as best illustrated in FIGS. 2C and 9. In this fully closed position, the front clip 10 has been latched closed about the blood vessel 200. Although the forward protuberance 164 of the escapement member 160 has been retracted below the base of the front clip, the front clip cannot be discharged from the instrument since it is still engaged by the jaws 112 and 111 which are squeezing the clip together. Further, the upper jaw 112 preferably has a receiving cavity 208 as best illustrated in FIGS. 8 and 9 for preventing forward movement of the clip beyond the position illustrated in FIG. 9 until the jaws are subsequently opened an amount sufficient to provide clearance between the upper jaw 112 and the clip protuberance 21.

FIG. 10 illustrates the jaws 111 and 112 being moved apart a distance sufficient to permit the latch closed front clip 10 to be discharged from the instrument. Specifically, the jaws 111 and 112 are opened an amount sufficient to permit the clip protuberance 21 to clear the upper jaw 112. Further, the entire instrument is moved rearwardly a small amount in the direction of the arrows 210 by the surgeon to permit the upper and lower jaws to completely clear the back of the clip 10 that is closed about the blood vessel 200.

When the jaws 111 and 112 are opened an amount sufficient to permit the discharge of the clip 10 from the instrument as illustrated in FIG. 10, the remaining clips in the row are urged forwardly by the pusher tape 128 to positively eject the front clip beyond the ends of the guideway flanges 124. As can be seen from FIG. 8, the front face 50 of the base of the second clip is initially disposed behind the rearward protuberance 166 of the escapement member 160 by a distance X. Preferably, the distance X is equal to the length of the leg rear section 41 (the rear section 41 being clearly illustrated in FIG. 1). Consequently, when the jaws 111 and 112 are opened sufficiently as illustrated in FIG. 10, the latched closed front clip is pushed forward the distance X by the next rearwardly adjacent clip until the base front face 50 of that next rearwardly adjacent clip is engaged by the upwardly projecting rearward protuberance 166 of the escapement member 160.

In view of the above description, and with reference to FIGS. 2B, 2C, 9, and 10, it should be apparent that the camming surfaces 184 function to maintain the rod 168 in the extreme rearward position during the last portion of the closing movement of the jaws as well as during the first portion of opening movement of the jaws. That is, the rod 168 is in the extreme rearward position just before the jaws are closed to the minimum spacing illustrated in FIG. 9 and also as the jaws are subsequently opened an amount sufficient to permit discharge of the latched closed clip. Thus, the escapement member 160 is maintained in the first orientation during the last portion of the closing movement of the handles as well as during the initial portion of the opening movement of the handles.

As the handles are opened still further, the jaws are necessarily moved away from each other by a greater amount as illustrated in FIG. 11. As this occurs, the camming surfaces 184 permit the cylindrical cam follower 180 to be biased forwardly by the spring 176 (FIG. 2B) to move the rod 168 forward and to thus pivot the escapement member 160 in the opposite direction so as to lower the rearward protuberance 166 and raise the forward protuberance 164. In the position illustrated in FIG. 11, the rearward protuberance 166 is being lowered to the point where it is almost, but not quite, clear of the clip base engaging face 50.

FIG. 12 illustrates the jaws 111 and 112 having been opened more than in FIG. 11 but not yet to the fully opened position. In this position, the rearward protuberance 166 has been retracted completely below the next clip base face 50 to permit the next clip to advance toward the jaw region. However, since the jaws are not fully opened, the top of the clip impinges against the upper jaw 112 and further movement of the clip forwardly into the jaw region is prevented.

When the jaws 111 and 112 are finally fully opened, the clip is free to be moved forward into the jaw region until the clip base face 50 is engaged by the raised forward protuberance 164 of the escapement member 160. When the jaws are thus fully opened, the clip would assume the same position illustrated for the front clip in FIG. 7.

By comparing FIG. 11 with FIG. 7, it can be seen that each clip is advanced forwardly a distance Y (FIG. 11) from the point of engagement with the escapement rearward protuberance 166 to the point of engagement with the escapement forward protuberance 164. This advancement occurs during the opening of the jaws after the front closed clip has been discharged.

With reference to FIG. 10 and the novel escapement and jaw structure described above, it is seen that each clip can be guided within the lower channel 122 beneath the flanges 124 without impeding the ejection of the clip after it has been latched closed. This is because the base flanges 52 (FIG. 1) extend only along the middle section of the clip leg and not along the rear section of the clip leg. Thus, as soon as the middle section of the clip has moved past the front end of the flanges 124, the clip is no longer positively retained within the instrument.

Further, since the clip base 45 (FIG. 1) does not extend forwardly beyond the middle section 42 of the clip leg, there is a recess below the front section 43 of the clip leg that accommodates the escapement member rearward protuberance 166 for effecting precise control of the forward progress of the clip as described above.

From the foregoing, it will be observed that numerous variations and modifications may be effected without departing from the true spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. A ligating clip adapted to be applied to tissue, each said clip comprising:
   first and second legs joined at their proximal ends by a resilient hinge to define the rear end of the clip and terminating at their distal ends at the front of the clip in latch means for holding the clip latched closed when the clip legs are squeezed together, each leg having a vessel clamping inner face in opposition to a vessel clamping inner face of the other leg;
   a base extending along a portion of said first leg, said base terminating short of the distal end of said first leg in a front face whereby an open recess is defined adjacent said base front face below said first leg; and
   flanges extending rearwardly along a portion of the length of said base from said base front face and terminating short of said first leg proximal end, said flanges extending laterally outwardly beyond the sides of the first leg, the portion of said base that extends along said first leg between said first leg proximal end and said flanges having a width not greater than the width of said first leg.

2. The clip in accordance with claim 1 wherein the portion of said base that extends along said first leg between said proximal end and said flanges has a generally right rectangular prism configuration.

3. The clip in accordance with claim 1 wherein the portion of said base with said flanges has a generally right rectangular prism configuration.

4. In a ligating clip adapted to be applied to tissue; each said clip comprising first and second legs joined at their proximal ends by a resilient hinge to define the rear end of the clip and terminating at their distal ends at the front of the clip in latch means for holding the clip latched closed when the clip legs are squeezed together, each leg having a vessel clamping inner face in opposition to a vessel clamping inner face of the other leg, the improvement characterized in that:
   said clip first leg has a (1) rear section extending forwardly from said hinge at said proximal end, (2) a front section extending rearwardly from the distal end of the first leg, and (3) a middle section connecting said front and rear sections;
   said clip includes a base extending along said rear and middle sections of said first leg, said base terminating in a front face below the juncture of said middle and front sections of said first leg whereby an open recess is defined adjacent said base front face below said first leg front section;
   said clip has flanges on said base along the length of said clip first leg middle section, said flanges extending laterally outwardly beyond the sides of the first leg; and
   the portion of said base along said first leg rear section has a width not greater than the width of said first leg.

5. The clip in accordance with claim 4 further characterized in that the portion of said base along said first leg rear section has a generally right rectangular prism configuration.

6. The clip in accordance with claim 4 further characterized in that said first leg terminates at the distal end thereof in a deflectable hook member extending from the vessel clamping inner face of said first leg, said hook member having an inner face spaced from and substantially parallel to the vessel clamping inner face of said first leg; and in that said second leg terminates at the distal end thereof in a surface adapted to deflect said hook member and enter the space between the inner face of said hook member and the vessel clamping inner face of said first leg whereby, when said first and second legs are pivoted closed about said hinge, the distal end of said second leg deflects and engages the hook member of said first leg to latch the clip closed.

7. The clip in accordance with claim 4 further characterized in that said second leg includes a boss.

8. The clip in accordance with claim 4 further characterized in that the portion of the base with said flanges along said first leg middle section has a generally right rectangular prism configuration.

9. A ligating clip adapted to be applied to tissue by an instrument that has an escapement to regulate the discharge of said clip from the instrument, each said clip comprising:
   first and second legs joined at their proximal ends by a resilient hinge to define the rear end of the clip and terminating at their distal ends at the front of the clip in latch means for holding the clip latched closed when the clip legs are squeezed together, each leg having a vessel clamping inner face in opposition to a vessel clamping inner face of the other leg;
   a base extending along a portion of said first leg, said base terminating short of the distal end of said first leg in a front face whereby an open recess is defined adjacent said base front face below said first leg to permit the positioning of said instrument escapement temporarily against said base front face; and
   flanges extending rearwardly along a portion of the length of said base from said base front face and terminating short of said first leg proximal end, said flanges extending laterally outwardly beyond the sides of the first leg to function as guide means for engaging portions of said instrument, the portion of said base with said flanges having a generally right rectangular prism configuration, the portion of said base that extends along said first leg between said first leg proximal end and said flanges having a generally right rectangular prism configuration with a width not greater than the width of said first leg to facilitate ejection of the latched closed clip from said instrument when said escapement is withdrawn.

10. In a ligating clip adapted to be applied to tissue by an instrument for holding and guiding a plurality of said clips, said instrument having an escapement to regulate the discharge of said clips from the instrument; each said clip comprising first and second legs joined at their proximal ends by a resilient hinge to define the rear end of the clip and terminating at their distal ends at the front of the clip in latch means for holding the clip latched closed when the clip legs are squeezed together, each leg having a vessel clamping inner face in opposition to a vessel clamping inner face of the other leg, the improvement characterized in that:
   said clip first leg has a (1) rear section extending forwardly from said hinge at said proximal end, (2) a front section extending rearwardly from the distal end of the first leg, and (3) a middle section connecting said front and rear sections;
   said clip includes a base extending along said rear and middle sections of said first leg, said base terminating in a front face below the juncture of said middle and front sections of said first leg whereby an open recess is defined adjacent said base front face below said first leg front section to permit the positioning of said instrument escapement temporarily against said base front face;
   said clip has flanges on said base along the length of said clip first leg middle section, said flanges extending laterally outwardly beyond the sides of the first leg to function as guide means for engaging portions of said instrument;
   the portion of the base with said flanges along said first leg middle section has a generally right rectangular prism configuration; and
   the portion of said base along said first leg rear section has a generally right rectangular prism configuration and has a width not greater than the width of said first leg to facilitate ejection of the latched closed clip from said instrument when said escapement is withdrawn.

11. The clip in accordance with claim 10 further characterized in that said first leg terminates at the distal end thereof in a deflectable hook member extending from the vessel clamping inner face of said first leg, said hook member having an inner face spaced from and substantially parallel to the vessel clamping inner face of said first leg; and in that said second leg terminates at the distal end thereof in a surface adapted to deflect said hook member and enter the space between the inner face of said hook member and the vessel clamping inner face of said first leg whereby, when said first and second legs are pivoted closed about said hinge, the distal end of said second leg deflects and engages the hook member of said first leg to latch the clip closed.

12. The clip in accordance with claim 10 further characterized in that said second leg includes a boss adapted to be engaged by a portion of said instrument.

* * * * *